United States Patent [19]

Khanna et al.

[11] Patent Number: 5,070,195

[45] Date of Patent: Dec. 3, 1991

[54] RING-OPENING PROCESS FOR PREPARATION OF 2-CHLOROSULFINYL AZETIDINONES

[75] Inventors: Jag M. Khanna; Naresh Kumar; Kiran Bala; Yatendra Kumar, all of New Delhi, India

[73] Assignee: Ranbaxy Laboratories Limited, New Delhi, India

[21] Appl. No.: 490,151

[22] Filed: Mar. 7, 1990

[30] Foreign Application Priority Data

Nov. 6, 1989 [IN] India ................................ CBR4500
Nov. 6, 1989 [IN] India ........................ 10191DEL/89

[51] Int. Cl.$^5$ ................... C07D 205/95; C07D 501/14; C07B 45/04
[52] U.S. Cl. .................................... 540/218; 540/359
[58] Field of Search ............................... 540/218, 359

[56] References Cited

U.S. PATENT DOCUMENTS 3,993,646  11/1976  Kamiya et al. .................. 540/358
4,091,210   5/1978  Kamiya et al. .................. 544/18
4,289,695   9/1981  Chou ............................... 540/359

Primary Examiner—Mark L. Berch
Attorney, Agent, or Firm—Marmorek, Guttman & Rubenstein

[57] ABSTRACT

An improved method for preparing 2-chlorosulfinyl azetidine-4-one comprises heating a penicillin sulfoxide ester with an N-chlorohalogenating agent at a temperature of about 75° C. to about 140° in an inert organic solvent, and in the presence of an organic solvent insoluble, strongly basic ion exchange resin. Desirably, the ion exchange resin comprises a styrene-divinyl benzene copolymer which is about 2 to 16% cross-linked and incorporates a quaternary ammonium functionality. Such ion exchange resins are commercially available. The 2-chlorosulfinyl azetidine-4-one which is produced by this method can be cyclized in the presence of a Friedel-Crafts catalysts to afford the 3-exomethylene cepham sulfoxide ester in yields of 80-90%.

18 Claims, No Drawings

RING-OPENING PROCESS FOR PREPARATION OF 2-CHLOROSULFINYL AZETIDINONES

BACKGROUND OF THE INVENTION

The present invention relates to an improved method for the preparation of 2-chlorosulfinyl azetidine-4-ones (II) from penicillin sulfoxide esters (I). In particular, it relates to an improvement in the first step of a two-step process for converting penicillin sulfoxide esters (I) via 2-chlorosulfinyl azetidine-4-one intermediates (II) to 3-exomethylene cepham sulfoxide esters (III).

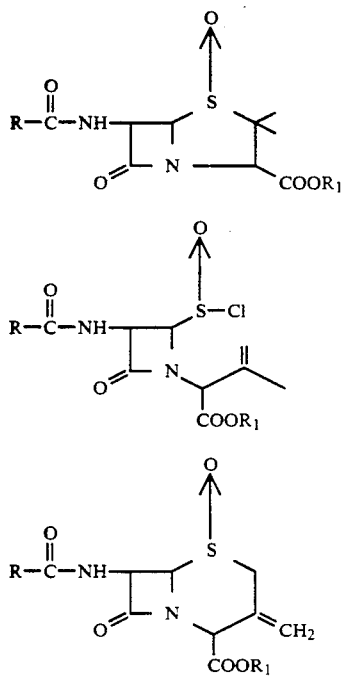

According to this invention, a sulfoxide ester (I) is reacted with an N-chlorohalogenating agent in the presence of a strongly basic ion exchange resin cross-linked with styrene-divinyl benzene copolymer to provide the corresponding 2-chlorosulfinyl azetidine-4-one (II). The improvement comprises the use of an ion exchange resin incorporating a quaternary ammonium functionality which removes hydrogen chloride formed in the reaction medium, thus preventing the formation of degradation products and hence giving overall higher yields. Commercial availability of the ion-exchange resins, their complete and easy removal from the reaction medium by simple filtration and their regeneration make this process commercially economical.

The 2-chlorosulfinyl azetidine-4-one compounds (II) are valuable intermediates in the preparation of 3-exomethylene cepham-4-carboxylic acid ester sulfoxides (III) which in turn are used in the manufacture of clinically useful antibacterial agents such as Cefaclor, Cefroxadine etc. These intermediate compounds (II) are prepared by the reaction of corresponding penicillin sulfoxide esters (I) with an N-chlorohalogenating agent such as N-chlorosuccinimide or N-chlorophthalimide in an inert organic solvent at 75°-140° C.

U.S. Pat. No. 4,052,387 (Oct. 4, 1977) and U.S. Pat. No. 4,081,440 (Mar. 28, 1978) by Kukolja describe a process for the preparation of 2-chlorosulfinyl azetidine-4-one (II) by treatment of the corresponding penicillin sulfoxide ester (I) with an N-chlorohalogenating agent in an inert organic solvent in the presence or absence of a non-alkaline acid scavenger such as propylene oxide, butylene oxide and the like to remove any hydrogen chloride formed in the reaction. Cyclization of the intermediate (II) with a Friedel-Crafts catalyst affords the corresponding 3-exomethylene cepham-4-sulfoxide ester (III) in an overall yield of 25-40% (with the exception of example 8 in U.S. Pat. No. 4,052,387).

Further, in U.S. Pat. No. 4,165,315 (Aug. 21, 1979), Kukolja describes a method similar to that of U.S. Pat. Nos. 4,052,387 and 4,081,440 for the preparation of 2-chlorosulfinyl azetidine-4-one (II) by using a non-alkaline acid scavenger such as propylene oxide which on cyclization with stannic chloride gives the exomethylene compound III in a very low yield (9-34%).

The method described in the above patents does not provide an economical, commercially viable process. When the reaction scale is increased beyond typical research laboratory quantities, for example in those instances where 50 grams or more of the penicillin sulfoxide ester has been used as a starting material, the results are poor.

In U.S. Pat. No. 4,075,203 (Feb. 21, 1978) and U.S. Pat. No. 4,165,316 (Aug. 27, 1979) Chou described an improved process for the preparation of 2-chlorosulfinyl azetidine-4-one intermediate (II) by carrying out the reaction of penicillin sulfoxide ester (I) with an N-chlorohalogenating agent in the presence of an alkylene oxide in combination with calcium oxide as a hydrogen chloride acceptor. The intermediate (II), on cyclization with a Lewis acid, affords 3-exomethylene cepham ester (III) with an overall yield varying between 32-59%.

Further improvement is reported in U.S. Pat. No. 4,289,695 (Sept. 15, 1981) by Chou, wherein the use of a weakly basic, organic solvent insoluble poly-(4-vinyl pyridine) polymer cross-linked with divinyl benzene as a hydrogen chloride binding agent has been used in the chlorinating step to give 2-chlorosulfinyl azetidine-4-one (II) which on cyclization with a Lewis acid gives the corresponding 3-exomethylene cepham sulfoxide ester (III) in an overall yield of 10-76%.

SUMMARY OF THE INVENTION

In accordance with the present invention, an improved method for the preparation of a 2-chlorosulfinyl azetidine-4-one of the formula

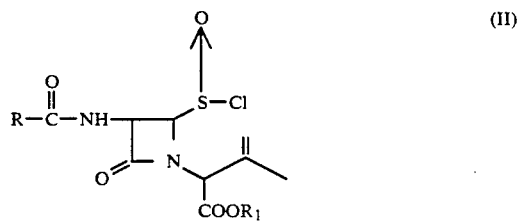

(II)

comprises, heating in an inert organic solvent a penicillin sulfoxide of the formula

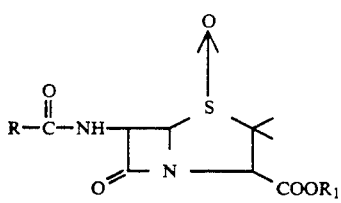

at a temperature between about 75° C. and about 140° C. with an N-chlorohalogenating agent in the presence of an organic solvent insoluble, strongly basic ion exchange resin. In the inventive process, R is hydrogen, $C_1$-$C_3$ alkyl, halomethyl or cyanomethyl;

or R is the group $R_3$ wherein $R_3$ is phenyl or phenyl substituted by $C_1$-$C_4$ alkyl, $C_1$-$C_4$ alkoxy, halo, protected hydroxy, nitro, cyano and trifluoromethyl;

or R is a group of the formula $$R_4-O-$$

wherein $R_4$ is a t-butyl, 2,2,2-trichloroethyl, benzyl or substituted benzyl;

or R is a group of the formula $$R_5-(O)_n-CH_2-$$

wherein $R_5$ is $R_3$ as defined above, 2-thienyl, 3-thienyl, 2-furyl, 3-furyl or 1,4-cyclohexadienyl, and n is 0 or 1;

or R is a substituted aryl alkyl group of the formula

wherein $R_6$ has the same meaning as $R_5$ defined above and W is protected hydroxy or protected amino; and $R_1$ is a carboxylic acid protecting group selected from the group consisting of $C_1$-$C_4$ alkyl, 2,2,2-trihalo alkyl, benzyl, substituted benzyl, phenacyl, halo substituted phenacyl and benzhydryl.

In a preferred embodiment, the strongly basic ion exchange resin comprises a styrene-divinyl benzene copolymer which is about 2 to about 16% cross-linked and includes a quaternary ammonium functionality, while the N-chlorohalogenating agent is selected from the group consisting of N-chloro urea, N-chloroamide, N-chloro urethan, N-chlorosulfonamide, N-chlorosulfimide, and N-chloroimide.

DETAILED DESCRIPTION OF THE INVENTION

According to the process of this invention, 6-acylamido-2,2-dimethyl-penam-3-carboxylic acid ester sulfoxide (I) is reacted with an N-chlorohalogenating agent in the presence of a strongly basic ion exchange resin at a temperature between 75° C. and 140° C., preferably between 100° C. and 135° C., in an inert organic solvent under anhydrous conditions to form the correspondingly substituted 2-chlorosulfinyl azetidine-4-one represented by the formula II. Friedel Crafts cyclization of the azetidinone intermediate (II) affords the corresponding 3-exomethylene compound in 80–90% yield.

Anion exchange resins (Type I and Type II) employed in the process of the present invention are high molecular weight polymers. Their strongly basic character is due to the presence of quaternary ammonium functionality. The anion exchangers used herein are based on styrene-divinyl benzene copolymer incorporating a quaternary ammonium functionality as an integral part of the polymer lattice and an equivalent amount of anions such as chloride, hydroxyl or sulphate ions. In Type I resins the four substituents on the nitrogen atom are a polymeric benzyl and three methyl groups. Type I resins are prepared by the reaction of trimethylamine with the copolymer followed by chloromethylation with chloromethyl methyl ether (CMME). In Type II resins one of the methyl groups of Type I is replaced by an ethanol group. Type II resins are prepared by using dimethyl ethanol amine instead of trimethylamine.

Type I

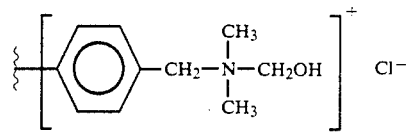

Type II

These strongly basic resins are inexpensive and commercially available. The cross linking with styrene-divinyl benzene ranges from about 2% to about 16%. The particle size of these resins varies from about 20 mesh to about 400 mesh. The following commercially available anion exchange resins containing quaternary ammonium functionality can be used in this process:

Dowex 1, Dowex 2, Dowex 11, and Dowex 21 K, available from Dow Chemical Co., Midland, Mich.; Amberlites IRA 400, IRA 410, and IRA 910, available from Rohm & Haas Co., Philadelphia, Pa.; Zerolit FF, available from Permutit Co., London, England; Duolite A-42, available from Diamond Alkali Co., Cleveland, Ohio; Lewatit M 5020 and M5080, available from Merck & Co. and Bayer A.G. of West Germany.

Improved yields of the 3-exomethylene compound (III) obtained in the present invention can be attributed to the rapid removal of hydrogen chloride formed in the reaction medium thus preventing the formation of side products. The resins being insoluble in the organic solvents used herein, can be easily removed by simple filtration and can be reused after regeneration.

An advantage of the present invention is that the resins are easily accessible in commercial lots and cheaper as compared with the cross-linked polymers reported in prior art (e.g., U.S. Pat. No. 4,289,695—Sept. 15, 1981) and thus making the present invention useful for industrial production.

$R_1$ in the above formulas denotes a carboxylic acid protecting group. Specific illustrations of the preferred carboxylic acid protecting groups of the sulfinyl chlorides of this invention include methyl, ethyl, n-propyl, isopropyl, n-butyl, isobutyl, sec-butyl, t-butyl, 2,2,2-trichloroethyl, 2,2,2-tribromoethyl, benzyl, p-nitrobenzyl, p-methoxybenzyl, benzhydryl, phenacyl, p-chlorophenacyl, p-bromophenacyl and the like. Highly preferred carboxylic acid protecting groups are methyl, benzyl, p-nitrobenzyl, p-methoxybenzyl, benzhydryl and 2,2,2-trichloroethyl.

R in the above formula II is the residue of a carboxylic acid such as hydrogen, $C_1$-$C_3$ alkyl, cyanomethyl or halomethyl; or R is the group $R_3$ in which $R_3$ is phenyl or phenyl substituted by $C_1$-$C_4$ alkyl, $C_1$-$C_4$ alkoxy, halo, protected hydroxy, nitro, cyano, trifluoromethyl;

or R is a group of the formmula $R_4$—O— wherein $R_4$ is t-butyl, 2,2,2-trichloroethyl, benzyl or substituted benzyl;

or R is a group of the formula $$R_5\text{—(O)}_n\text{—CH}_2\text{—}$$

wherein $R_5$ has the same meaning as $R_3$ defined above, 1,4-cyclohexadienyl, 2-thienyl, 3-thienyl, 2-furyl, 3-furyl; n is 0 or 1;

or R is a substituted arylalkyl group of the formula

wherein $R_6$ is the same as $R_5$ and W is protected hydroxy or protected amino.

By the term N-chlorohalogenating agent, is meant a reagent having at least one chlorine bonded directly to a nitrogen atom with the remaining moiety or moieties of the structure of the reagent having a strong electron-withdrawing effect. The by-product corresponding to the N-chlorohalogenating agent after the chlorine atom has been replaced by a hydrogen atom is essentially inert to the sulfinyl chloride product. Several types of N-chlorohalogenating compounds as defined above include:

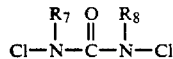 (IV)

where $R_7$ is hydrogen, chloro, $C_1$-$C_3$ alkyl, cyclohexyl, phenyl or phenyl substituted with chloro, bromo, methyl or nitro and $R_8$ is $C_1$-$C_3$ alkyl, cyclohexyl, phenyl or phenyl substituted with chloro, bromo, methyl or nitro;

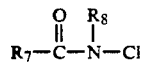 (V)

in which $R_7$ and $R_8$ are as defined above;

N-chloro urethans (VI)

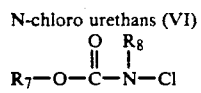 (VI)

wherein $R_7$ and $R_8$ are as defined above;

N-chloro sulfonamides (VII)

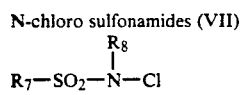 (VII)

wherein $R_7$ and $R^8$ are as defined above;

N-chloro sulfimides (VIII)

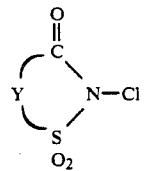 (VIII)

wherein Y is O-phenylene or —$(CH_2)_n$— in which n is 2 or 3; and

N-chloroimides (IX)

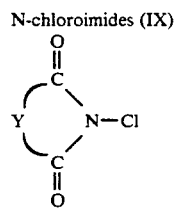 (IX)

wherein Y is the same as defined above.

N-chlorohalogenating agents which are preferred for use in the process of this invention are N-chloroimides, particularly N-chlorosuccinimide or N-chlorophthalimide.

The inert organic solvent in the present process refers to an aprotic organic solvent which does not react appreciably with either the N-chlorohalogenating agent or the 2-chlorosulfinylazetidine-4-one (II). Suitable inert organic solvents are those having a boiling point at least as high as the temperature of the reaction and include the aromatic hydrocarbons such as benzene, toluene, ethylbenzene, cumene, xylenes, tetralin and the like; the halogenated hydrocarbons such as carbon tetrachloride, chloroform, dichloroethane, 1,1,2-trichloroethane, ethylene dibromide and aromatic ethers such as anisole, diphenylether and the like. Preferred organic solvents of this process are benzene, toluene and xylenes. Reagent grade solvents are preferably used and are suitably dried.

According to the present invention the reaction of penicillin sulfoxide ester (I) with N-chlorinating agent in the presence of strongly basic ion exchange resin in a suitable inert organic solvent at 75° C. to 140° C. is carried out to produce the corresponding 2-chlorosulfinyl azetidine-4-one (II). Generally from about 1 mole to about 1.6 moles of the halogenating agent is used per 1 mole of the starting material. The ratio of the ion exchange resin to penicillin sulfoxide ester (I) ranges between 1:1 to 1:5 by weight. The preferred ratio being 1:3 by weight of said resin to sulfoxide ester.

The invention is further illustrated by reference to the comparative examples which follow. It is not intended that this invention be limited in scope by reason of any of the examples provided herein.

EXAMPLE 1 p-Nitrobenzyl 3-Methyl-2-(2-Chlorosulfinyl-4-Oxo-3-Phenoxyacetamido-1-Azetidinyl)-3-Butenoate 5 g of Dowex 1×16 (100–200 mesh), a Type I anion exchange resin (16% cross-linked with divinyl benzene (DVB)), was suspended in 300 ml of dry toluene. Moisture of the resin and of toluene was removed by azeotropic distillation using Dean-stark water trap. The mixture was cooled to 25° C. 10 g of p-nitrobenzyl-6- phenoxyacetamido-2,2-dimethylpenam-3-carboxylate-1-oxide and 5 g of N-chlorophthalimide were added. The reaction mixture was refluxed for ½ hours and then cooled to 10° C. The insoluble material was filtered and the filtrate w. concentrated to dryness to provide 10.13 g (95%) of the title compound.

IR (CHCl₃): cm⁻¹ 1790, 1750, 1700, 1530, 1350, 1220, 1040.

¹H NMR (CDCl₃): δ 1.90(s,3H), 4.53(s,2H), 5.13(m,3H), 5.3(s,2H), 5.55, (d,1H), 6.05(dd,1H) and 6.6-8.05(m,9H).

EXAMPLE 2 p-Nitrobenzyl 7-Phenoxyacetamido-3-Exomethylene Cepham-4-Carboxylate-1-Oxide 5 g of Dowex 1×16 (100-200 mesh) was suspended in 300 ml of toluene. Moisture was removed by azeotropic distillation using Dean-Stark water tap. The solvent was cooled to 25° C. and 10 g of p-nitrobenzyl 6-phenoxyacetamido-2,2-dimethylpenam-3-carboxylate-1-oxide and 5.4 g of N-chlorophthalimide were added. The reaction mixture was refluxed for 1½ hours. After the completion of the reaction, the mixture was cooled to 10° C. and insoluble material was filtered. To the filtrate was added 2 ml of diethyl ether followed by the addition of 5 ml of stannic chloride in 10 ml of toluene at 0° C. After half a hour stirring at 0° C., the orange colored complex thus formed was further stirred at 10° C. for 4 hr. The complex was filtered and washed with 50 ml of hexane. Stirring of this complex in 80 ml methanol at 5° C. gave the off-white precipitate which was stirred for another 2 hr. The product was filtered and dried. Yield 8.94 g (90%), mp 192°-194° C. ¹H NMR (CDCl₃): δ 3.6 (q,2H), 4.5(s,2H), 4.83(d,1H), 5.3(s,2H), 5.33(s,1H), 5.5(s,1H), 5.78(s,1H), 6.02(dd,1H) and 6.9-8.3(m,9H). Anal Calcd. C,H,N for C₂₃H₂₁N₃O₈S(499.5): C,55.31; H,4.24; N,8.41%. Found: C, 55.40; H, 4.12; N, 8.44%.

EXAMPLE 3 p-Nitrobenzyl 7-Phenylacetamido-3-Exomethylene Cepham-4-Carboxylate-1-Oxide 2.5 g of Dowex 1×16 (100-200 mesh) was suspended in 150 ml of toluene. Moisture was removed by azeotropic distillation through Dean-Stark water trap. The contents were cooled to 25° C. followed by the addition of 5 g of p-nitrobenzyl 6-phenylacetamido-2,2-dimethylpenam-3-carboxylate-1-oxide and 2.43 g of N-chlorophthlimide. The reaction mixture was refluxed for about 1½ hours and allowed to cool to 10° C. The insoluble material thus separated was removed by filtration. The filtrate was further cooled to 0° C. and 1 ml of diethyl ether was added followed by the addition of 2.5 ml of stannic chloride. After ½ hr stirring at 0° C., the brown colored complex was formed, stirred at 10° C. for 6 hrs and kept overnight at the same temperature. The complex was filtered and washed with 25 ml of hexane. After addition of the complex in 40 ml methanol at 5° C., the light yellow precipitate separated out. It was stirred for 2 hrs at 5° C. The product was filtered and dried. Yield 4.22 g (80.5%), mp 206°-208° C., ¹H NMR (CDCl₃): δ 3.3-3.8(m,4H); 5.3(d,1H); 5.25(s,3H); 5.45(s,1H); 5.75(s,1H); 6.0(dd,1H); 6.9(d,1H) and 7.2-8.4(m,9H).

EXAMPLE 4 p-Nitrobenzyl 7-Phenoxyacetamido-3-Exomethylene Cepham-4-Carboxylate-1-Oxide 2.5 g of Dowex 2×8, a Type II anion exchange resin 8% cross-linked with DVB (200-400 mesh) was suspended in 150 ml of toluene, moisture was removed by azeotropic distillation using Dean-Stark water trap. The solvent was cooled to room temperature and 5 g of p-nitrobenzyl 6-phenoxyacetamido-2,2-dimethylpenam-3-carboxylate-1-oxide and 2.70 g of N-chlorophthalimide were added. The reaction mixture was refluxed for 100 minutes. After the completion of the reaction, the mixture was cooled to 10° C. and insoluble material was filtered. To the filtrate was added 1 ml of dry ether followed by the addition of 2.5 ml of stannic chloride in 5 ml toluene at 0° C. After ½ hr stirring at 0° C., the complex was further stirred at room temperature for 3 hr. The complex was filtered, washed with 25 ml of hexane and added to 80 ml methanol at 5° C. The off-white precipitate immediately separated out. After 2 hrs stirring at 5° C., the product was filtered, washed and dried. Yield: 4.02 g (81%), mp 192°-193° C.

EXAMPLE 5 p-Nitrobenzyl 7-Phenoxyacetamido-3-Exomethylene Cepham-4-Carboxylate-1-Oxide 5 g of Dowex 1×16 (100-200 mesh) was heated in 300 ml of toluene and subjected to azeotropic distillation using Dean-Stark apparatus. After the complete removal of moisture, the contents were cooled to room temperature followed by the addition of 10 g of p-nitrobenzyl 6-phenoxyacetamido-2,2-dimethylpenam-3-carboxylate-1-oxide and 3.7 g of N-chlorosuccinimide. The reaction mixture was refluxed for about 1½ hr. After the completion of the reaction, the mixture was cooled to 10° C. and filtered. To the filtrate was added 2 ml of diethyl ether followed by the addition of 5 ml of stannic chloride in 10 ml of toluene at 0° C. After 1½ hr stirring at 0° C., an insoluble complex was formed which was further stirred for 4 hr, filtered and washed with 50 ml of hexane. It was added to 80 ml of methanol at 5° C. The off-white precipitate immediately separated out, stirring was continued for another 2 hr. The product was filtered and dried. Yield 7.99 g (80.4%).

EXAMPLE 6 p-Nitrobenzyl 7-Phenylacetamido-3-Exomethylene Cepham-4-Carboxylate-1-Oxide 4 g of Dowex 1×16 (100-200 mesh) was suspended in 300 ml of toluene and subjected to azeotropic distillation using Dean-Stark apparatus. The contents were cooled and 10 g p-nitrobenzyl 6-phenylacetamido-2,2-dimethylpenam-3-carboxylate-1-oxide and 3.7 g of N-chlorosuccinimide were added. The reaction proceeded as in Example 5. Yield 7.94 g (80%).

EXAMPLE 7

2,2,2-Trichloroethyl 3-Methyl-2-[2-Chlorosulfinyl-4-Oxo-3-Phenoxyacetamido-1-Azetidinyl]-3-Butanoate 1.75 g of Dowex 2×8 (200-400 mesh) was allowed to reflux in 100 ml of toluene to remove water by using Dean-Stark water tap. The heat was continued and 3.5 g of 2,2,2-trichloroethyl 6-phenoxyacetamido-2,2-dimethylpenam-3-carboxylate-1-oxide and 1.77 g N- chlorophthalimide were added at room temperature. The reaction mixture was heated at the reflux temperature for 1½ hr and was then cooled to about 10° C. The insoluble material was filtered off and the filtrate was concentrated to dryness to provide 95% of the title product.

EXAMPLE 8

2,2,2-Trichloroethyl 7-Phenoxyacetamido-3-Exomethylene Cepham-4-Carboxylate-1-Oxide 0.62 g of Dowex 2×8 (200–400 mesh) was suspended in 37 ml toluene and was subjected to azeotropic distillation using Dean-Stark water trap. The heat was discontinued and 1.24 g of 2,2,2-trichloroethyl 6-phenoxyacetamido-2,2-dimethylpenam-3-carboxylate-1-oxide and 0.63 g N-chlorophthalimide were added at room temperature. The reaction mixture was heated at the reflux temperature for 1½ hr and was then cooled to about 10° C. The insoluble material was filtered and the filtrate was further cooled to 0° C. 0.24 ml diethyl ether was added followed by the addition of 0.62 ml of stannic chloride in 1.24 ml toluene under stirring. Stirring was continued for 30 minutes at 0° C. and for another 3 hr at room temperature. The complex was filtered and washed with 6 ml hexane. The resulting complex was added to 10 ml methanol at 5° C. with stirring. After stirring for about 4 hr, the volume of methanol was reduced to one-third. Ethyl acetate was added. The organic layer was washed with 5% aqueous sodium bicarbonate, water and then dried over sodium sulphate. The solvent was removed to give 2,2,2-trichloroethyl-7-phenoxyacetamido-3-exomethylene cepham-4-carboxylate-1-oxide. Yield 0.98 g (80%); mp 140°–143° C.

EXAMPLE 9

Benzhydral 3-Methyl-2-(2-Chlorosulfinyl-4-Oxo-3-Phenoxyacetamido-1-Azetidinyl)-3-Butenoate 2.1 g of Dowex 1×16 (100–200 mesh) was refluxed in 125 ml toluene and moisture was removed by Dean-Stark apparatus. After cooling the mixture to 30°–35° C., 4.2 g of benzhydral 6-phenoxyacetamido-2,2-dimethylpenam-3-carboxylate-1-oxide and 2 g of N-chlorophthalimide were added. The mixture was refluxed for 1½ hr and then cooled to 10° C. The insoluble material was filtered and the filtrate was concentrated to dryness to give the title product in 97% yield.

$^1$H NMR (CDCl$_3$): δ 1.88 (s,3H), 4.53(s,2H), 4.90(s,1H), 5.14(s,2H), 5.54(s,1H), 6.24(q,1H), 6.95(s,1H), 7.15–7.40(m,15H), 8.0(d,1H).

EXAMPLE 10

Benzhydral 7-Phenoxyacetamido-3-Exomethylene Cepham-4-Carboxylate-1-Oxide 1.33 g of Dowex 1×16 (100–200 mesh) was refluxed in 80 ml toluene and moisture was removed by Dean-Stark apparatus. After cooling the mixture to 30°–35° C., 2.66 g of benzhydral 6-phenoxyacetamido-2,2-dimethylpenam-3-carboxylate-1-oxide and 1.27 g of N-chlorophthalimide were added. The mixture was then heated at the reflux temperature for 1½ hour. The dark suspension was cooled to 10° C. and filtered to remove polymer and phthalimide. The filtrate containing benzhydral-3-methyl-2-(2-chlorosulfinyl-4-oxo-3-phenylacetamido-1-azetindinyl-3-butanoate was cooled to 0° C. and 0.53 ml dry ether was added followed by 1.25 ml of stannic chloride in 3 ml toluene. The complex which formed was stirred for 30 minutes at 0° C. and for 4 hr at room temperature. It was filtered, washed with 14 ml of hexane and was then slowly added to 22 ml of methanol to precipitate the product benzhydral-7-phenoxyacetamido-3-exomethylene cepham-4-carboxylate-1-oxide. After 2 hr stirring, it was filtered and air dried. Yield 2.16 g (82%).

EXAMPLE 11 p-Nitrobenzyl 7-Phenoxyacetamido-3-Exomethylene Cepham-4-Carboxylate-1-Oxide 0.6 g of Dowex 2×8 (200–400 mesh) was suspended in 120 ml toluene. Moisture was removed by azeotropic distillation using Dean-Stark apparatus. The heating was stopped and 4 g of p-nitrobenzyl 6-phenoxyacetamide-2,2-dimethylpenam-3-carboxylate-1-oxide and 2.16 g of N-chlorophthalimide were added at room temperature. The reaction mixture was refluxed for 1½ hr. cooled to 10° C. and filtered. 0.8 ml of dry diethyl ether was added followed by the addition of 2 ml stannic chloride dry diethyl at 0° C. After ½ hr stirring at 0° C., the complex was stirred at room temperature for 3 hr. The complex was filtered, washed with 20 ml hexane and added to 32 ml methanol at 5° C. with stirring. The precipitate separated out after 2 hr stirring at 5° C., filtered and air dried. Yield 0.79 g (20%).

EXAMPLE 12 p-Nitrobenzyl 7-Phenoxyacetamido-3-Exomethylene Cepham-4-Carboxylate-1-Oxide

By employing the procedure as directed in Example 11, the reaction was carried out using 8 g of Dowex 2×8 (200–400 mesh) for 4 g of starting material. Usual work up gave 0.99 g (25%) of the title product.

EXAMPLE 13 p-Nitrobenzyl 7-Phenoxyacetamido-3-Exomethylene Cepham-4-Carboxylate-1-Oxide 5 g of Dowex 21K (20–50 mesh) was suspended in 300 ml of toluene and subjected to azeotropic distillation using Dean-Stark apparatus. After the complete removal of water, the contents were cooled to room temperature and 10 g of p-nitrobenzyl 6-phenoxyacetamido-2,2-dimethylpenam-3-carboxylate-1-oxide and 5.4 g of N-chlorophthalimide were added. The reaction mixture was refluxed for ½ hr. After the completion of the reaction, the mixture was cooled to 10° C. and insoluble material was filtered. To the filtrate was added 2 ml of diethyl ether followed by the addition of 5 ml of stannic chloride in 10 ml toluene at 0° C. After ½ hr stirring at 0° C., the complex was further stirred at room temperature for 3 hr. The complex was filtered, washed with 50 ml of hexane and added to 80 ml methanol at 5° C. with stirring. The precipitate, which separated out immediately, was stirred for another 2 hr and the product was filtered and air dried. Yield 8.0 g (80.5%) mp 192°–194° C.

EXAMPLE 14 p-Nitrobenzyl 7-Phenoxyacetamido-3-Exomethylene Cepham-4-Carboxylate-1-Oxide 2.5 g of Amberlite IRA 400 (20–50 mesh) was suspended in 150 ml of dry toluene. Moisture of Amberlite and toluene was removed by azeotropic distillation using Dean-Stark apparatus. The heating was stopped and 5 g of p-nitrobenzyl 6-phenoxyacetamido 2,2-dimethylpenam-3-carboxylate-1-oxide and 2.7 g of N-chlorophthalimide were added at room temperature. The reaction mixture was refluxed for 1½ hr, cooled to 10° C. and filtered. 1 ml of dry diethyl ether was added to the filtrate followed by the addition of 2.5 ml stannic chloride at 0° C. After half an hour stirring at 0° C., a brown colored complex was formed, which was stirred at room temperature for 3 hr, filtered and washed with hexane. The complex was added to 80 ml methanol and stirred for 2 hr. The off-white precipitate thus separated was filtered, washed with methanol and dried. Yield 4.05 g (81.5%).

EXAMPLE 15 p-Nitrobenzyl 7-Phenoxyacetamido-3-Exomethylene Cepham-4-Carboxylate-1-Oxide 5 g of Dowex 11 (20–50 mesh) was suspended in 300 ml of toluene and subjected to azeotropic distillation using Dean-Stark apparatus. After the complete removal of moisture, the contents were cooled and 10 g of p-nitrobenzyl 6-phenoxyacetamido-2,2-dimethylpenam-3-carboxylate-1-oxide and 5.4 g of N-chlorophthalimide were added. The same reaction conditions were followed as given in the example 5. Yield 8.05 g (81%), mp 192°–195° C.

EXAMPLE 16 p-Nitrobenzyl 7-Phenoxyacetamido-3-Exomethylene Cepham-4-Carboxylate-1-Oxide 3.5 g of Amberlite IRA 401 (20–50 mesh) was suspended in 180 ml toluene. Moisture of Amberlite and toluene was removed by azeotropic distillatoin using Dean-Stark apparatus. The heating was stopped. The contents were cooled to room temperature and 6 g of p-nitrobenzyl 6-phenoxyacetamido-2,2-dimethypanam-3-carboxylate-1-oxide and 3.24 g N-chlorophthalimide were added. The reaction mixture was refluxed for 1½ hr and was cooled to 10° C. The mixture was filtered and 1 ml of dry ether was added to the filtrate followed by the addition of 3 ml of stannic chloride in 6 ml toluene at 0° C. After ½ hr stirring at 0° C., the complex was stirred at room temperature for about 3 hr and was filtered. It was washed with 30 ml hexane and added in 80 ml methanol at 5° C. The contents were stirred for 2 hr at the same temperature. The off-white precipitate thus separated was filtered, washed with methanol and dried. Yield 4.83 g (81%).

While the invention has been described by reference to specific examples, this was for purposes of illustration only and should not be construed to limit the spirit or scope of the invention. Numerous alternative embodiments that are within the scope of the invention will be apparent to those skilled in the art.

We claim:

1. A process of preparing a 2-chlorosulfinylazetidine-4-one of the formula

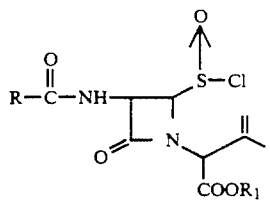

wherein R is hydrogen, $C_1$–$C_3$ alkyl, halomethyl or cyanomethyl;

or R is the group $R_3$ wherein $R_3$ is phenyl or phenyl substituted by $C_1$–$C_4$ alkyl, $C_1$–$C_4$ alkoxy, halo, protected hydroxy, nitro, cyano and trifluoromethyl;

or R is a group of the formula $$R_4-O-$$

wherein $R_4$ is a t-butyl, 2,2,2-trichloroethyl, benzyl or substituted benzyl;

or R is a group of the formula $$R_5-(O)_n-CH_2-$$

wherein $R_5$ is $R_3$ as defined above, 2-thienyl, 3-thienyl, 2-furyl, 3-furyl or 1,4-cyclohexadienyl, and n is 0 or 1;

or R is a substituted aryl alkyl group of the formula $$R_6-\underset{W}{\underset{|}{CH}}-$$

wherein $R_6$ has the same meaning as $R_5$ defined above and W is protected hydroxy or protected amino; and $R_1$ is a carboxylic acid protecting group selected from the group consisting of $C_1$–$C_4$ alkyl, 2,2,2-trihalo alkyl, benzyl, substituted benzyl, phenacyl, halo substituted phenacyl and benzhydryl, which comprises heating in an inert organic solvent a penicillin sulfoxide ester of the formula

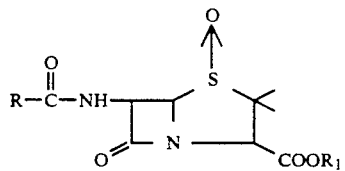

wherein R and $R_1$ are as defined above at a temperature between about 75° C. and about 140° C. with an N-chlorohalogenating agent in the presence of an organic solvent insoluble, strongly basic ion exchange resin, wherein said ion exchange resin incorporates a quaternary ammonium functionality.

2. The process of claim 1 wherein said ion exchange resin comprises a styrene-divinyl benzene copolymer.

3. The process of claim 1 wherein R is $C_6H_5CH_2$ or $C_6H_5OCH_2$, and $R_1$ is benzyl, p-nitrobenzyl, p-methoxybenzyl, benzhydryl or 2,2,2-trichlorethyl.

4. The process of claim 1 wherein said ion exchange resin is a Type I anion exchange resin.

5. The process of claim 1 wherein said ion exchange resin is a Type II anion exchange resin.

6. The process of claim 1 wherein said ion exchange resin comprises a styrene-divinyl benzene copolymer that is about 2 to about 16% cross-linked.

7. The process of claim 1 wherein said ion exchange resin is selected from the group consisting of Dowex, Amberlite, Zerolit, Duolite, and Lewatit resins.

8. The process of claim 1 wherein said N-chlorohalogenating agent is selected from the group consisting of N-chloro urea, N-chloroamide, N-chloro urethan, N-chlorosulfonamide, N-chlorosulfimide, and N-chloroimide.

9. The process of claim 8 wherein said N-chlorohalogenating agent is an N-chloroimide of the formula

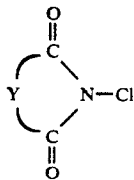

wherein Y is O-phenylene or —$(CH_2)_n$— in which n is 2 or 3.

10. The process of claim 1 wherein said N-chlorohalogenating agent is N-chlorosuccinimide or N-chlorophthalimide.

11. The process of claim 1 wherein said inert solvent is an aromatic organic solvent.

12. The process of claim 11 wherein said inert solvent is selected from the group consisting of benzene, toluene, and xylene.

13. The process of claim 1 wherein said inert solvent is a halogenated hydrocarbon.

14. The process of claim 13 wherein said inert solvent is selected from the group consisting of carbon tetrachloride, chloroform, dichloroethane, and 1,1,2-trichloroethane.

15. A process for preparing a 3-exomethylene cepham sulfoxide ester of the formula

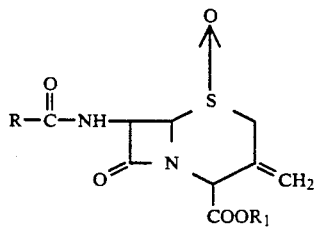

which comprises preparing a 2-chlorosulfinylazetidin-4-one as set forth in claim 1, and cyclizing said 2-chlorosulfinylazetidin-4-one.

16. The process of claim 15 wherein said 2-chlorosulfinylazetidin-4-one is cyclized by contacting it with a Friedel-Crafts catalyst.

17. The process of claim 15 wherein said Friedel-Crafts catalyst is a Lewis acid.

18. The process of claim 16 wherein said Lewis acid is stannic chloride.

* * * * *